United States Patent [19]

Imai

[11] 4,221,738

[45] Sep. 9, 1980

[54] PRODUCTION OF ACRYLONITRILE

[75] Inventor: Tamotsu Imai, Mt. Prospect, Ill.

[73] Assignee: UOP Inc., Des Plaines, Ill.

[21] Appl. No.: 18,371

[22] Filed: Mar. 5, 1979

[51] Int. Cl.$^2$ .................. C07C 120/00; C07C 121/32
[52] U.S. Cl. .......................... 260/465.9; 252/466 PT; 252/474
[58] Field of Search ...................... 260/465.9; 252/474

[56] References Cited

U.S. PATENT DOCUMENTS

| | | | |
|---|---|---|---|
| 3,308,193 | 3/1967 | Bajars | 260/465.9 X |
| 3,531,543 | 9/1970 | Clippinger et al. | 252/466 PT X |
| 3,535,402 | 10/1970 | Kluksdahl | 252/474 X |
| 3,649,565 | 3/1972 | Wilhelm | 252/466 PT |
| 3,682,838 | 8/1972 | Block | 252/474 X |
| 3,878,131 | 4/1975 | Hayes | 252/466 PT |
| 4,003,852 | 1/1977 | Hayes | 252/466 PT |
| 4,125,565 | 11/1978 | Antos | 252/474 X |

*Primary Examiner*—Dolph H. Torrence
*Attorney, Agent, or Firm*—James R. Hoatson, Jr.; Raymond H. Nelson; William H. Page, II

[57] ABSTRACT

Acrylonitrile may be prepared by dehydrogenating propionitrile in the presence of dehydrogenation catalysts comprising a nonacidic complex containing a Group VIII metal and at least one metal selected from Groups IVA, VA, and VIIB of the Periodic Table. If so desired, the catalyst may also include a metal from Group IA or IIA of the Periodic Table and the combination may be supported on inorganic materials. The catalyst may be exemplified by platinum, tin and lithium composited on alumina.

13 Claims, No Drawings

PRODUCTION OF ACRYLONITRILE

This invention relates to a process for the production of acrylonitrile. More specifically, the invention is concerned with the process for producing acrylonitrile by dehydrogenating propionitrile in the presence of certain catalytic compositions of matter of the type hereinafter set forth in greater detail.

Acrylonitrile which is also known as vinyl cyanide will find a wide variety of uses in the chemical industry. For example, it may be used in the preparation of synthetic rubber, plastics, fibers such as those known under the tradenames of Acrilan, Dynel, Orlon, etc. In addition, the compound is also used in other organic synthesis, in the paper industry and as a grain fumicant. Various processes have been evolved to prepare this particular compound. For example, acrylonitrile may be prepared by the addition of hydrogen cyanide to acetylene in the presence of cuprous chloride catalysts. However, an apparent and overt disadvantage to this process is the instability and inherent danger which is present when working with both hydrogen cyanide and acetylene. Another method of preparing acrylonitrile is by the catalytic dehydration of ethylene cyanohydrin or from the reaction of propylene, air and ammonia. In contradistinction to these methods, it has now been discovered that acrylonitrile may be prepared by testing propionitrile in a dehydrogenation reaction in which the reaction is effected in the presence of certain catalytic compositions of matter to form the desired compound.

It is therefore an object of this invention to provide a process for the preparation of acrylonitrile.

A further object of this invention is to provide a process for the production of acrylonitrile whereby economical attractive yields of the desired product are obtained.

In one aspect an embodiment of this invention resides in a process for the preparation of acrylonitrile which comprises treating propionitrile in the presence of a dehydrogenation catalyst comprising a nonacidic complex containing a Group VIII metal and at least one metal selected from Groups IVA, VA and VIIB of the Periodic Table composited on a porous carrier material at dehydrogenation conditions, and recovering the resultant acrylonitrile.

A specific embodiment of this invention is found in a process for the preparation of acrylonitrile which comprises treating propionitrile in the presence of a dehydrogenation catalyst comprising a nonacidic complex of platinum, tin and lithium composited on alumina at a temperature in the range of from about 400° to about 700° C. and a pressure in the range of from about 0.5 to about 10 atmospheres, and recovering the resultant acrylonitrile.

Other objects and embodiments will be found in the following detailed description of the present invention.

As hereinbefore set forth the present invention is concerned with the process for producing acrylonitrile by treating propionitrile with a dehydrogenation catalyst at dehydrogenation conditions. The dehydrogenation of propionitrile is effected by contacting propionitrile at dehydrogenation conditions with a nonacidic catalytic composite of the type hereinafter set forth in greater detail. Dehydrogenation conditions which are employed to effect the desired production will include temperatures which are selected from the range of from about 400° to about 700° C. and a pressure which may range from about 0.5 up to about 10 atmospheres. When superatmospheric pressures are employed, the pressures will be afforded by the presence of hydrogen or an inert gas such as nitrogen, helium, argon, etc. It is also contemplated that a combination of hydrogen and an inert gas may be employed in which the hydrogen will afford only a partial pressure of the desired operating pressure, the remainder consisting of the inert gas.

The dehydrogenation of propionitrile is effected in the presence of a nonacidic catalyst composite which contains a Group VIII metal and at least one element selected from Groups IVA, VA and VIIB of the Periodic Table composited on a porous carrier material. In addition, if so desired, a metal selected from Groups IA and IIA of the Periodic Table may also be added to the catalyst to neutralize the acidity of the porous carrier materials which are used. These nonacidic multimetallic catalytic composites will possess improved activity and stability characteristics. Examples of metals of Group VIII of the Periodic Table which comprise one component of the catalyst composite will preferably include platinum, palladium, iridium, nickel, and well as osmium, ruthenium, and rhodium. Examples of Group IA and IIA of the Periodic Table will include lithium, sodium, potassium, rubidium, cesium, magnesium, calcium, strontium, while elements of Groups IVA, VA and VIIB which may be employed will include in particular germanium, tin, lead, arsenic, antimony, bismuth and rhenium. In a preferred embodiment, the nonacidic catalytic composite will contain, on an elemental basis, about 0.01 to about 2 wt. % of the metal of Group VIII, from about 0.01 to about 5 wt. % of the alkali or alkaline earth metal and from about 0.01 to about 5 wt. % of the Group IVA, VA and VIIB elements, said components being uniformly dispersed throughout the porous carrier material, wherein substantially all of the metal components are present in the corresponding elemental metallic states and wherein substantially all of the Group IVA, VA and VIIB component and the alkali or alkaline earth metal component are present in an oxidation state above that of the elemental metal.

As hereinbefore set forth, the multimetallic components are composited on a porous carrier material. It is preferred that this material be a porous, adsorptive, high surface area support having a surface area of about 25 to about 500 m$^2$/g. The porous carrier material should be relatively refractory to the conditions utilized in the dehydrogenation process and it is intended to include within the scope of the present invention carrier materials which have traditionally been utilized in hydrocarbon conversion catalysts such as: (1) activated carbon, coke or charcoal; (2) silica or silica gel, silicon carbide, clays and silicates including those synthetically prepared and naturally occurring, which may or may not be acid treated for example, attapulgus clay, china clay, diatomaceous earth, fuller's earth, kaolin, kieselguhr, etc.; (3) ceramics, porcelain, crushed firebrick, bauxite; (4) refractory inorganic oxides such as alumina, titanium dioxide, zirconium dioxide, chromium oxide, zinc oxide, magnesia, thoria, boria, silica-alumina, silica-magnesia, chromia-alumina, alumina-boria, silica-zirconia, etc.; (5) crystalline zeolitic aluminosilicates such as naturally occurring or synthetically prepared mordenite and/or faujasite, either in the hydrogen form or in a form which has been treated with multivalent cations; and, (6) combinations of elements from one or more of these groups. The preferred porous carrier materials for use in the present invention are refractory inorganic oxides, with best results obtained with an alumina carrier material. Suitable alumina materials are the crystalline aluminas known as the gamma-, eta- and theta-aluminas, with gamma-alumina giving best results. In addition, in some embodiments, the alumina carrier material may contain minor proportions of other well-known refractory inorganic oxides such as silica, zirconia, magnesia, etc.; however, the preferred support is substantially pure gamma-alumina. Preferred carrier materials have an apparent bulk density of about 0.2 to about 0.8 g/cc and surface area characteristics such that the average micropore diameter measured by nitrogen adsorption is about 20 to 300 Angstroms, the pore volume is about 0.1 to 1 cc/g and the surface area is about 10 to about 500 $m^2/g$. In general, excellent results are typically obtained with a gamma-alumina carrier material which is used in the form of spherical particles having: a relatively small diameter (i.e. typically about 1/16 inch), an apparent bulk density of about 0.3 g/cc, a pore volume of about 0.5 cc/g and a surface area of about 170 $m^2/g$.

The preferred alumina carrier material may be prepared in any suitable manner and may be prepared in a synthetic manner or may be naturally occurring. However, the alumina to be employed may be activated prior to use by one or more treatments including drying, calcination, steaming, etc. For example, the alumina carrier may be prepared by adding a suitable alkaline reagent, such as ammonium hydroxide, to a salt of alumina such as aluminum chloride in such an amount to form an aluminum hydroxide gel which, upon drying or calcining, is converted to alumina. The alumina carrier may be formed in any desired shape such as spheres, pills, cakes, extrudates, powders, granules, etc. A particularly preferred form of alumina is the sphere; and these spheres may be continuously manufactured by the well-known oil drop method which comprises the steps of: (1) forming an alumina hydrosol by any of the techniques taught in the art and preferably by reacting alumina metal with hydrochloric acid; (2) combining the resulting hydrosol with a suitable gelling agent; (3) and dropping the resultant mixture into an oil bath which is maintained at elevated temperatures. The droplets of the mixture remain in the oil bath until they set and form hydrogen spheres, said spheres then being continuously withdrawn from the oil bath and typically subjected to specific aging treatments in oil and an ammoniacal solution to further improve their physical characteristics. The resulting aged and gelled particles are then washed and dried at a relatively low temperature of from about 300° to about 400° F. followed by a calcination procedure at a temperature of about 850° to about 1300° F. for a period of from about 1 to about 20 hours. In the preferred procedure, the calcined particles are subjected to a high temperature treatment with steam in order to remove undesired acidic components such as any residual chloride. This method affects conversion of the alumina hydrogel to the corresponding crystalline gamma-alumina.

One component of the multimetallic catalyst comprises an element of Group IVA, VA and VIIB of the Periodic Table such as germanium, tin, arsenic, antimony, bismuth, rhenium, or lead. Substantially all of the Group IVA, VA and VIIB elements will be present in the final catalyst in an oxidation state above that of the elemental metal. This component may be present in chemical combination with one or more of the other ingredients of the composite, or as a chemical compound of germanium, tin or lead such as the oxide, sulfide, halide, oxyhalide, oxychloride, aluminate, etc., compounds, the preferred form of the compound being that of the corresponding oxide. This component is preferably present in the final composite in an amount in the range of from about 0.01 to about 5 wt. % thereof, calculated on an elemental basis, the most preferred amount being from about 0.05 to about 2 wt. %. This component may be incorporated in the composite in any suitable manner known in the art, the end result being in a uniform dispersion of the moiety throughout the carrier material, such a coprecipitation or cogelation with the porous carrier material, ion exchange with the carrier material or impregnation of the carrier material at any stage in its preparation. For example, one method of incorporating this component into the composite involves the utilization of a soluble decomposable compound of the Group IVA metal to impregnate the porous carrier material either before, during or after the carrier material is calcined. The solvent which is used during this impregnation step is selected on the basis of its capability to dissolve the desired compound without effecting the porous carrier material which is to be impregnated; good results being obtained when water is the solvent and thus the preferred compound for use in this impregnation step is typically water-soluble and decomposable. Regardless of which impregnation solution is utilized, the component may be impregnated either prior to, simultaneously with, or after the other metallic components are added to the carrier material.

A second metallic component of the multimetallic catalytic composite includes a metal of Group VIII of the Periodic Table such as platinum, palladium, ruthenium, rhodium, osmium, iridium or nickel. This component will generally comprise about 0.01 to about 2 wt. % of the final catalytic composite calculated on an elemental basis and the metal will exist within the final catalytic composite in the elemental metallic state. This component may also be incorporated in the catalytic composite in any suitable method known to result in a relatively uniform distribution of this component in the carrier material, said methods including coprecipitation, cogelation, ion exchange or impregnation. Again, as in the case of the Group IVA metal component of the catalyst, one method of preparing the composite involves the utilization of a soluble, decomposable compound to impregnate the carrier material in a relatively uniform manner. For example, as an illustration thereof this component may be added to the support by commingling said support with an aqueous solution of chloroplatinic or chloropalladic acid. Another method for incorporating this component into the catalytic composite comprises cogelling or coprecipitating the components such as iridium during the preparation of the carrier material. This is accomplished by the use of a soluble, decomposable compound of iridium such as chloroiridic acid or iridium tetrachloride to the alumina hydrosol before it is gelled. Thereafter the resulting mixture is then finished by conventional gelling, aging, drying and calcination steps.

Another component of the multimetallic catalytic composite which is utilized to dehydrogenate a dehydrogenatable hydrocarbon is a compound of Groups IA or IIA of the Periodic Table, that is, an alkali or alkaline earth component. In the preferred embodiment, this component is selected from the groups consisting of compounds of the alkali metals, namely, cesium, rubidium, potassium, sodium and lithium and of the alkaline earth metals, namely, calcium, strontium, barium and magnesium. This component exists within the catalytic composite in an oxidation state above that of the elemental metal such as a relatively stable compound including the oxide or sulfide, or in combination with one or more of the other components of the composite, or in combination with the carrier material such as for example, in the form of a metal aluminate. The amount of this component is preferably selected to provide a nonacidic composite containing from about 0.1 to about 5 wt. % of the alkali or alkaline earth metal, and more preferably, from about 0.25 to about 3.5 wt. %. In the preferred embodiment this component of the multimetallic catalyst composite will be a compound of lithium or potassium. The function of this component is to neutralize any of the acidic material which may have been used in the preparation of the catalyst in order to insure that the final catalyst composite is nonacidic in nature. Again, as in the case of the previously mentioned metallic components of the catalyst composite, the alkali or alkaline earth component may be combined with the porous carrier material in any manner known to those skilled in the art in order to result in a relatively uniform dispersion of this component throughout the carrier material with a subsequent neutralization of any acidic sites which may be present thereon. Best results are ordinarily obtained when this component is added to the carrier material in a step subsequent to the addition of the other metallic components inasmuch as the alkali metal or alkaline earth metal acts to neutralize the acid used in the preferred impregnation procedure for these metallic components. For example, the Group VIII metal component and the Group IVA metal component may be added to the carrier material and the resulting composite oxidized in a stream of air at a high temperature in the range of from about 600° to about 1000° F. following which the resulting oxidized component is treated with steam or a mixture of air and steam in order to remove at least a portion of any residual acidity, and thereafter add the alkali metal or alkaline earth metal component.

It is also contemplated within the scope of this invention that the catalyst composite may also be subjected to a presulfiding step. In this step the catalyst is subjected to the presence of sulfur for a predetermined period of time at an elevated temperature. Generally speaking, the catalyst may be treated with a stream of gas which comprises a mixture of hydrogen sulfide and hydrogen for a period of time ranging from about 1 to about 10 hours at a temperature in the range of from about 400° to about 600° C. The gas mixture will usually comprise from about 1 to about 5% hydrogen sulfide and from about 99% to about 95% hydrogen.

The process of the present invention is effected by contacting the propionitrile with the nonacidic multimetallic catalytic composite of the type hereinbefore set forth in greater detail in a dehydrogenation zone at dehydrogenation conditions. The contact of the propionitrile with the catalytic composite may be accomplished by using the catalyst in a fixed bed system, a moving bed system, a fluidized bed system or in a batch type operation. In the preferred embodiment the catalyst is disposed as a fixed bed in a dehydrogenation zone and the propionitrile feed stream which, if so desired, may have been preheated by any suitable means to the desired reaction temperature is passed into said zone. It is, of course, understood that the dehydrogenation zone may be one or more separate reactors with suitable heating means therebetween to insure that the desired conversion temperature is maintained at the inlet to each reactor. The propionitrile may be contacted with the catalyst bed in either an upward, downward or radial flow phase and may be in the liquid phase, a mixed liquid-vapor phase or a vapor phase in contact with the catalyst, the best results being obtained when utilizing a vapor phase reactor.

Although hydrogen is the preferred diluent for use in the reaction, it is also contemplated within the scope of this invention that other art recognized diluents such as steam, methane, carbon dioxide, and the like may also be advantageously utilized. In the preferred embodiment of the invention, hydrogen is utilized due to the fact that it serves the dual function of not only lowering the partial pressure of the propionitrile but also suppresses the formation of hydrogen-deficient carbonaceous deposits on the catalytic composite. Ordinarily, hydrogen is utilized in amounts sufficient to insure a hydrogen to propionitrile mole ratio of from about 1:1 to about 20:1, with best results being obtained in the range of from about 1.5:1 to about 10:1. The effluent from the reactor is continuously withdrawn and subjected to conventional means of separation whereby the desired acrylonitrile may be separated from any unreacted propionitrile and/or unwanted side reaction products which may have been formed, and recovered.

The following examples are given for purposes of illustrating the process of the present invention and the use of the desired catalytic compositions of matter. However, it is to be understood that these examples are given merely for purposes of illustration and that the present process is not necessarily limited thereto.

EXAMPLE I

In the first example 5.50 grams of a catalyst consisting of 0.364% platinum, 0.52% tin, and 0.55% lithium supported on an alumina base which possess an ABD of 0.3 was placed in a 1" diameter stainless steel reactor. The inlet temperature of the reactor during the reaction period was about 557° C. A stream of propionitrile was charged to the reactor at a liquid hourly space velocity of 0.65 hr.$^{-1}$ along with a stream of hydrogen, the hydrogen to propionitrile molar feed ratio being 7.4. The dehydrogenation of the propionitrile took place over a period of 260 minutes. The results of this run are set forth in Table I below.

TABLE I

| Time On Stream (Min.) | Propionitrile Conversion (%) | Selectivities (Mol %) | | | |
|---|---|---|---|---|---|
| | | ACN$^a$ | AN$^b$ | HCN$^c$ | Others$^d$ |
| 70 | 18.7 | 40.4 | 13.4 | 8.2 | 38.0 |
| 140 | 13.4 | 62.9 | 5.6 | 4.3 | 27.2 |
| 200 | 12.5 | 66.8 | 3.4 | 2.7 | 27.1 |
| 260 | 10.4 | 77.0 | 3.1 | 2.0 | 17.9 |

$^a$Acrylonitrile
$^b$Acetonitrile
$^c$Hydrogen cyanide
$^d$Major products were $C_1$-$C_3$ hydrocarbons

EXAMPLE II

In this example 5.65 grams of a catalyst similar in composition to that used in Example I above but which had been presulfided at a temperature of 510° C. for a period of 6 hours using a 1% hydrogen sulfide-99% hydrogen gas stream was placed in the reactor. The inlet temperature of the reactor was maintained at 564°

C. while propionitrile was passed to the reactor at a liquid hourly space velocity of 0.50 hr.$^{-1}$. In addition, hydrogen was also passed to the reactor at a rate of 9.4 moles of hydrogen per mole of propionitrile. The dehydrogenation reaction was effected for a period of 327 minutes with the results being set forth in Table II below:

TABLE II

| Time On Stream (Min.) | Propionitrile Conversion (%) | Selectivities (Mol %) | | | |
|---|---|---|---|---|---|
| | | ACN | AN | HCN | Others |
| 83 | 17.3 | 46.6 | 11.9 | 6.2 | 35.3 |
| 143 | 16.4 | 67.3 | 6.1 | 2.4 | 24.2 |
| 201 | 11.6 | 74.9 | 3.6 | 1.2 | 20.3 |
| 270 | 9.8 | 81.2 | 2.8 | — | 16.0 |
| 327 | 9.3 | 83.0 | 2.2 | — | 14.8 |

EXAMPLE III

To illustrate the efficiency of the catalysts set forth in the present invention as contrasted to other dehydrogenation catalysts, another experiment was performed in which 5.1 grams of a catalyst consisting only of 0.375 wt. % platinum supported on an alumina base having an ABD of 0.3 was placed in the reactor. The inlet temperature of the reactor was maintained at 556° C. while propionitrile was charged to the reactor at a liquid hourly space velocity of 0.75 hr.$^{-1}$ along with hydrogen in an amount of 3.2 moles of hydrogen per mole of propionitrile. The reaction was effected for a period of 190 minutes, the results of this run being set forth in Table III below.

TABLE III

| Time On Stream (Min.) | Propionitrile Conversion (%) | Selectivities | | | |
|---|---|---|---|---|---|
| | | ACN | AN | HCN | Others |
| 77 | 20.2 | 25.8 | 18.6 | 7.6 | 48.0 |
| 135 | 14.4 | 41.3 | 12.4 | 5.7 | 40.6 |
| 190 | 11.8 | 51.9 | 7.3 | 4.5 | 36.3 |

It is to be noted from a comparison of the results obtained in Examples I and II above with the results obtained in this experiment, that the catalysts described in the present invention exhibited a much greater selectivity to the desired acrylonitrile while maintaining similar propionitrile conversions. In addition, the selectivities to undesired products when using the catalyst of the present invention were much lower than that which was obtained when using the platinum on alumina catalyst.

I claim as my invention:

1. A process for the preparation of acrylonitrile which comprises contacting propionitrile at dehydrogenation conditions with a dehydrogenation catalyst comprising a nonacidic complex containing, on an elemental basis, from about 0.01 to about 2 wt. % of a Group VIII metal and from about 0.01 to about 5 wt. % of a metal from Groups IVA, VA and VIIB of the Periodic Table composited on a porous carrier material, and recovering the resultant acrylonitrile.

2. The process as set forth in claim 1 further characterized in that said catalyst contains, on an elemental basis, from about 0.01 to about 5 wt. % of an alkali or alkaline earth metal.

3. The process as set forth in claim 1 in which said dehydrogenation conditions include a temperature in the range of from about 400° to about 700° C. and a pressure in the range of from about 0.5 to about 10 atmospheres.

4. The process as set forth in claim 1 in which said porous carrier material is an alumina.

5. The process as set forth in claim 4 in which said alumina is gamma-alumina.

6. The process as set forth in claim 1 in which said porous carrier material is silica-alumina.

7. The process as set forth in claim 1 in which said catalyst is platinum, tin, and lithium composited on alumina.

8. The process as set forth in claim 2 in which said catalyst comprises platinum and lithium.

9. The process as set forth in claim 1 in which said catalyst comprises platinum and tin.

10. The process as set forth in claim 1 further characterized in that said process is effected in the presence of hydrogen.

11. The process as set forth in claim 1 in which said catalyst is subjected to a sulfiding step prior to use.

12. The process as set forth in claim 11 in which said sulfiding step is effected at a temperature in the range of from about 400° to about 600° C.

13. The process as set forth in claim 11 in which said sulfiding step is effected by treating said catalyst with a stream of gas containing hydrogen sulfide.

* * * * *